United States Patent [19]

Beriger et al.

[11] Patent Number: 4,861,787
[45] Date of Patent: Aug. 29, 1989

[54] NEMATICIDAL COMPOSITIONS

[75] Inventors: Ernst Beriger, Allschwil, Switzerland; Wolfgang Eckhardt, Lörrach, Fed. Rep. of Germany; Robert Nyfeler, Basel, Switzerland

[73] Assignee: Ciba-Geigy Corporation, Ardsley, N.Y.

[21] Appl. No.: 263,961

[22] Filed: Oct. 25, 1988

Related U.S. Application Data

[63] Continuation of Ser. No. 95,728, Sep. 14, 1987, abandoned.

[30] Foreign Application Priority Data

Sep. 26, 1986 [CH] Switzerland .......................... 3870/86

[51] Int. Cl.$^4$ .................. C07D 417/04; C07D 413/04; A01N 43/82
[52] U.S. Cl. .................................... 514/363; 514/364; 548/136; 548/144
[58] Field of Search ................ 548/136, 144; 514/363, 514/364

[56] References Cited

U.S. PATENT DOCUMENTS 2,744,908  5/1956  Young .................................. 548/136
4,694,014  9/1987  Beriser ................................. 514/363

FOREIGN PATENT DOCUMENTS 8607590  12/1986  World Int. Prop. O. .......... 548/129

OTHER PUBLICATIONS

Orerte, Ann Chim 53 1687 (1963), abstract.

*Primary Examiner*—Robert Gerstl
*Attorney, Agent, or Firm*—Edward McC. Roberts

[57] ABSTRACT

Novel compounds of the formula

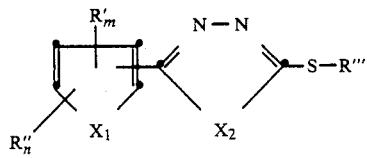

in which
R' represents $C_1$-$C_5$-alkyl, halogen, trifluoromethyl or $C_1$-$C_3$-alkoxy;
R" represents $C_1$-$C_5$-alkyl or halogen; and
R''' represents $C_1$-$C_5$-alkyl that is unsubstituted or is substituted by from 1 to 6 halogen atoms, $C_1$-$C_5$-alkenyl that is unsubstituted or is substituted by from 1 to 6 halogen atoms, or $C_1$-$C_5$- alkynyl that is unsubstituted or is substituted by from 1 to 6 halogen atoms;
m represents 0, 1, 2 or 3 and
n represents 0 or 1; and
$X_1$ and $X_2$ each represents, independently of the other, oxygen or sulphur, as active ingredients for controlling plant parasite nematodes and for preventing damage to cultivated plants caused by nematode attack.

9 Claims, No Drawings

NEMATICIDAL COMPOSITIONS

This application is a continuation of application Ser. No. 095,728, filed 9/14/87, now abandoned.

The present invention relates to novel substituted 2-mercapto-5-furyl-1,3,4-oxadiazole and 2-mercapto-5-furyl-1,3,4-thiadiazole derivatives, and also 2-mercapto-5-thienyl-1,3,4-oxadiazole and 2-mercapto-5-thienyl-1,3,4-thadiazole derivatives, to the preparation thereof and to nematocidal compositions containing as active ingredient at least one of those compounds. The invention also relates to the use of the novel active ingredients and compositions for the control of nematodes, especially nematodes that damage plants.

The compounds according to the invention correspond to the general formula I

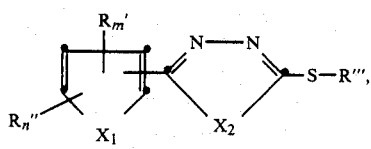

in which
R′ represents $C_1$–$C_5$-alkyl, halogen, trifluoromethyl or $C_1$–$C_3$-alkoxy;
R″ represents $C_1$–$C_5$-alkyl or halogen; and
R‴ represents $C_1$–$C_5$-alkyl that is unsubstituted or is substituted by from 1 to 6 halogen atoms, $C_1$–$C_5$-alkenyl that is unsubstituted or is substituted by from 1 to 6 halogen atoms, or $C_1$–$C_5$-alkynyl that is unsubstituted or is substituted by from 1 to 6 halogen atoms;
m represents 0, 1, 2 or 3 and
n represents 0 or 1; and
$X_1$ and $X_2$ each represents, independently of the other, oxygen or sulphur.

Alkyl, as an independent radical or as a part of another group, such as alkoxy, is to be understood as a straight-chain or branched alkyl group. This includes the methyl and ethyl group and the isomers of the propyl, butyl and pentyl group, and of these especially methyl, ethyl, n-propyl, isopropyl, isobutyl or n-pentyl. Halosubstituted alkyl is a mono- to per-halogenated alkyl radical, such as, for example, $CHCl_2$, $CH_2F$, $CCl_3$, $CH_2Cl$, $CHFCH_3$, $CH_2CH_2Br$, $CF_2CF_3$, $C_2Cl_5$, $CH_2Br$, $CHBrCl$ etc., and is preferably $CF_3$ or $CHF_2$. Alkenyl is, for example, propen-1-yl, allyl, buten-1-yl, buten-2-yl or buten-3-yl and chains with several double bonds. Alkynyl is, for example, propyn-2-yl, butyn-1-yl, butyn-2-yl, pentyn-4-yl etc., but is preferably propargyl. Halogen is fluorine, chlorine, bromine or iodine, preferably fluorine, chlorine or bromine.

Oxadiazole and thiadiazole derivatives that have been described as nematocidally active are already known. Such compounds with a 1,2,4-position of the hetero atoms are disclosed in U.S. Pat. Specification No. 3,770,754, whilst U.S. Pat. Specification No. 4,454,147 describes 1,3,4-thiadiazole derivatives in which, compared with the compounds of the invention, the heterocycle instead of the mercapto groups is substituted by a chlorine atom. These known compounds have hitherto, as nematocides, not been able fully to meet the demands made upon them in practice. Also, oxadiazole derivatives with a fungicidal activity are described in DE-OS No. 2 361 613. There is not, however, mentioned *expressis verbis* therein any of those compounds that fall within the scope of formula I according to the invention.

By making available the compounds of formula I according to the invention it is now possible to make a valuable contribution to controlling plant nematodes that cause considerable agricultural damage to the crop. In the manner it is possible for losses in yield in cultivated plants such as, for example, potatoes, cereals, beets, rape, cabbage, tobacco, soybeans, cotton and vegetatbles, and damge in tree nurseries and in ornamental plant nurseries to be checked effectively. The compounds according to the invention are distinguished especially by their effective control of root parasite soil nematodes such as, for example, those of the genera Heterodera and Globodera (cyst-forming nematodes), Meloidogyne (root knot nematodes) and of the genera Radopholus, Pratylenchus, Tylenchulus, Longidorus, Trichodorus, and Xiphinema. It is also possible with the active ingredients of the invention effectively to control the nematode genera Ditylenchus (stem parasites), Aphelenchoides (leaf nematodes) and Anguina (blossom nematodes).

With the active ingredients of the formula I it is preferably possible successfully to control especially harmful species of nematodes of the genus Meloidogyne, such as, for example, *Meloidogyne incognita*, and of the genus Heterodera, such as, for example, *Heterodera glycines* (soybean cyst nematode) and also of the genus Globodera, such as, for example, *Globodera rostochiensis* (potato cyst nematode) and also representatives of migrating endoparasites, such as, for example, *Pratylenchus penetrans* or *Radopholus similis* and representatives of ectoparasites, such as, for example, Trichodorus spp. and Xiphinema spp..

The novel active ingredients can be used curatively, preventatively or systemically to control plant nematodes and to keep the crop healthy. They have a broad spectrum of activity against the various species of nematodes and consequently meet the practical requirements. The nematocidal mode of action of the compounds of the invention is advantageously accompanied by a low phytotoxicity so that the general desirability of a reduction in pollution of the environment is achieved to a substantial extent.

Within the scope of the present invention, the following compound groups of the formula I are preferred:
(1) compounds in which
R′ represents $C_1$–$C_5$-alkyl, halogen, trifluoromethyl or $C_1$–$C_3$-alkoxy;
R″ represents $C_1$–$C_5$-alkyl or halogen; and
R‴ represents $C_1$–$C_5$-alkyl that is unsubstituted or is substituted by from 1 to 6 halogen atoms, $C_1$–$C_5$-alkenyl that is unsubstituted or is substituted by from 1 to 6 halogen atoms, or $C_1$–$C_5$-alkynyl that is unsubstituted or is substituted by from 1 to 6 halogen atoms;
m represents 0, 1, 2 or 3 and
n represents 0 or 1; and
$X_1$ and $X_2$ each represents, independently of the other, oxygen or sulphur,
with the proviso that when m and n together represent 0 or when $X_1$ represents sulphur and R′ and R″ together represent 3 chlorine atoms, R‴ may not be alkenyl or alkynyl.

(2) Compounds in which
R′ represents $C_1$–$C_2$-alkyl, halogen, trifluoromethyl or $C_1$–$C_2$-alkoxy;
R″ represents $C_1C_2$-alkyl or halogen;

R''' represents $C_1$-$C_3$-alkyl that is unsubstituted or is substituted by from 1 to 3 halogen atoms, $C_1$-$C_3$-alkenyl that is unsubstituted or is substituted by from 1 to 3 halogen atoms, or $C_1$-$C_3$-alkynyl that is unsubstituted or is substituted by from 1 to 3 halogen atoms;

m represents 0, 1 or 2 and n represents 0 or 1; and $X_1$ and $X_2$ each represents, independently of the other, oxygen or sulphur.

(3) Compounds in which

R' represents $C_1$-$C_2$-alkyl, halogen, trifluoromethyl or $C_1$-$C_2$-alkoxy;

R'' represents $C_1$-$C_2$-alkyl or halogen;

R''' represents $C_1$-$C_3$-alkyl that is unsubstituted or is substituted by from 1 to 3 halogen atoms, $C_1$-$C_3$-alkenyl that is unsubstituted or is substituted by from 1 to 3 halogen atoms, or $C_1$-$C_3$-alkynyl that is unsubstituted or is substituted by from 1 to 3 halogen atoms;

m represents 0, 1 or 2, and n represents 0 or 1; and $X_1$ and $X_2$ each represents, independently of the other, oxygen or sulphur, with the proviso that when m and n together represent 0 or when $X_1$ represents sulphur and R' and R'' together represent 3 chlorine atoms, R''' may not be alkenyl or alkynyl.

(4) Compounds in which

R' represents methyl, chlorine, bromine or methoxy;

R'' represents methyl, chlorine, bromine or iodine;

R''' represents $C_1$-$C_3$-alkyl that is unsubstituted or is substituted by from 1 to 3 fluorine atoms, $C_1$-$C_3$-alkenyl that is unsubstituted or is substituted by from 1 to 3 fluorine atoms, or $C_1$-$C_3$-alkynyl that is unsubstituted or is substituted by from 1 to 3 fluorine atoms;

m and n each represents, independently of the other, 0 or 1; and $X_1$ and $X_2$ each represents, independently of the other, oxygen or sulphur.

(5) Compounds in which

R' represents methy, chlorine, bromine or methoxy;

R'' represents methyl, chlorine, bromine or iodine;

R''' represents $C_1$-$C_3$-alkyl that is unsubstituted or is substituted by from 1 to 3 fluorine atoms, $C_1$-$C_3$-alkenyl that is unsubstituted or is substituted by from 1 to 3 fluorine atoms, or $C_1$-$C_3$-alkynyl that is unsubstituted or is substituted by from 1 to 3 fluorine atoms;

m and n each represents, independently of the other, 0 or 1; and $X_1$ and $X_2$ each represents, independently of the other, oxygen or sulphur, with the proviso that when m and n together represent 0 or when $X_1$ represents sulphur and R' and R'' together represent 3 chlorine atoms, R''' may not be alkenyl or alkynyl.

(6) Compounds in which

R' represents methyl, chlorine, bromine or methoxy;

R'' represents methyl, chlorine, or bromine; and

R''' represents $C_1$-$C_3$-alkyl that is unsubstituted or is substituted by from 1 to 3 fluorine atoms;

m and n each represents, independently of the other, 0 or 1; and $X_1$ and $X_2$ each represents, independently of the other, oxygen or sulphur.

(7) Compounds in which

R' represents methyl, chlorine, bromine or methoxy;

R'' represents methyl, chlorine or bromine; and

R''' represents $CHF_2$; and m and n each represents, independently of the other, 0 or 1; and $X_1$ and $X_2$ each represents, independently of the other, oxygen or sulphur.

The following compounds are preferred:

2-difluoromethylthio-5-thien-2-yl-1,3,4-thiadiazole, 2-difluoromethylthio-5-(5-chlorothien-2-yl)-1,3,4-thiadiazole, 2-difluoromethylthio-5-(5-methylthien-2-yl)-1,3,4-thiadiazole, 2-difluoromethylthio-5-(5-bromothien-2-yl)-1,3,4-thiadiazole, 2-difluoromethylthio-5-thien-2-yl-1,3,4-oxadiazole, 2-difluoromethylthio-5-(chlorothien-2-yl)-1,3,4,-oxadiazole, 2-difluoromethylthio-5-(5-methylthien-2-yl)-1,3,4-oxadiazole, 2-difluoromethylthio-5-(furan-2-yl)-1,3,4-thiadiazole, 2-difluoromethylthio-5-(2-methylfuran-3-yl)-1,3,4-thiadiazole, 2-difluoromethylthio-5-(4-methylthien-2-yl)-1,3,4-thiadiazole, 2-difluoromethylthio-5-(furan-2-yl)-1,3,4-oxadiazole.

Compounds of the formula I are prepared in accordance with the invention as follows:

(a) in a condensation reaction, a compound of the formula IIa

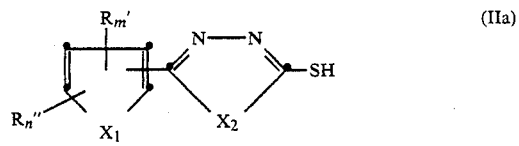
(IIa)

or a compound of the formula IIb

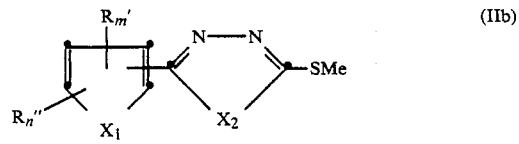
(IIb)

is reacted with a compound of the formula IIIa

(IIIa)

in an inert solvent or mixture of solvents at elevated temperature, optionally in the presence of a catalyst and optionally at elevated pressure, the reaction of a compound of the formula IIa being carried out in the presence of a base, or (b) in an addition reaction, a compound of the formula IIa

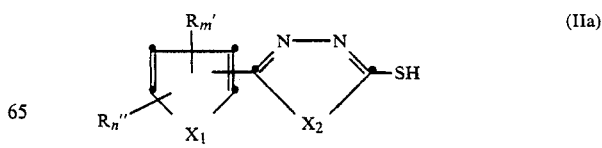
(IIa)

is reacted with a compound of the formula IIIb

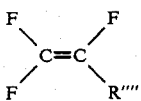  (IIIb)

in an inert solvent or mixture of solvents at elevated temperature, optionally in the presence of a catalyst and optionally at elevated pressure, this reaction resulting in a compound of the formula Ia

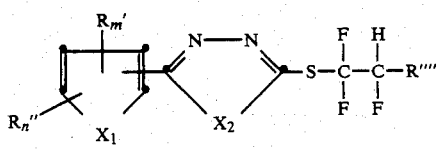  (Ia)

or a compound of the formula Ib

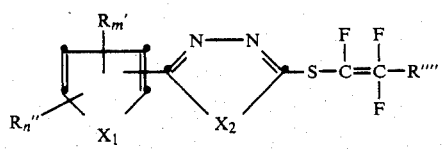  (Ib)

In the above formulae IIa, IIB, Ia, Ib, IIIa and IIIB, Me represents an alkali metal or amminium, Hal represents halogen, preferably chlorine, bromine or iodine, and R'''' represents fluorine or trifluoromethyl, whilst R', R'', R''', m, n, $X_1$ and $X_2$ are as defined for formula I.

Suitable solvents or diluents for the preparation of the active ingredients of the invention are, for example, ethers and ethereal compounds such as dialkyl ethers (diethyl ether, diisopropyl ether, tert.-butylmethyl ether etc.), anisole, dioxan and tetrahydrofuran; aliphatic and aromatic hydrocarbons such as benzene, toluene and petroleun ether; halogenated hydrocarbons such as chlorobenzene, methylene chloride, chloroform, ethylene chloride, carbon tetrachloride and tetrachloroethylene; nitriles such as acetonitrile and propionitrile; N,N-dialkylated amides such as dimethylformamide; dimethyl sulphoxide; ketones such as acetone, diethyl ketone, methyl ethyl ketone and also water and alcohols such as, for example, methanol, ethanol, isopropanol or butanol; and, quite generally, mixtures of such solvents with one another.

Suitable bases are organic and inorganic bases, for example preferably tertiary amines such as trialkylamines (trimethylamine, triethylmaine, tripropylamine etc.), and also oxides, hydroxides, carbonates and hydrogen carbonates of alkali metals and alkaline earth metals (for example CaO, BaO, NaOH, KOH, $Ca(OH)_2$, $KHCO_3$, $NaHCO_3$, $Ca(HCO_3)_2$, $K_2CO_3$, $Na_2CO_3$ etc.), and also acetates such as, for example, $CH_3COONa$ or $CH_3COOK$. Also suitable as bases are alkali alcoholates such as, for example, sodium ethoxide, sodium propoxide, potassium tert.-butoxide or sodium methoxide.

The addition of catalytic amounts of a Crown ether such as, for example, 18-Crown-6- or 15-Crown-5-, has a favourable effect on the course of the reaction in the preparation process. Also, the catalytic use of tetraalkylamine salts, for example tetraalkylammonium hydrochlorides or hydrobromides, preferably tetra-n-butylammonium hydrobromide, has proved advantageous for the same purpose. Furthermore, alkali iodides, preferably potassium iodide, may advantageously be used as catalysts.

The reaction temperatures in the preparation processes are from 10° to 90° C., preferably from 30° to 80° C. Pressures of from 1 to 20 bars, preferably from 6 to 14 bars, are standard for the pressure conditions during the course of the reaction.

The invention relates also to compositions for the control of nematodes that damage plants, and for the prevention of attack on the crop by nematodes, that contain the active ingredients of the formula I.

Furthermore, the present invention includes, in addition, the preparation of nematocidal compositions which is characterised by the intimate mixing of active ingredients of the formula I with one or more carriers and adjuvants described herein. Also included is a method for the treatment of plants which is characterised by the application of the compounds of the formula I or the novel compositions.

Some of the starting compounds of the formula IIa and IIB are known. The novel compounds of the said formulae are intermediates for the preparation of valuable nematocidal active ingredients (see Table O) and therefore the present invention relates also to these.

The starting compounds of the formula IIa and IIB may be prepared according to known methods, as follows:

(a) 2-Mercapto-1,3,4-oxadiazoles can be obtained by adding carbon disulphide to a solution of the correspondingly substituted furoyl or thenoyl hydrazide in aqueous alcoholic potassium hydroxide and heating the reaction mixture for a few hours. The solvents used for this are alcohols such as, for example, ethyl alcohol or n-amyl alcohol. The free mercapto compounds are obtained by acidifying the resulting potassium salts [see J. Am. Chem. Soc. 78, 4975–4978 (1956)].

(b) 2-Mercapto-1,3,4-thiadiazoles can be obtained by treating the correspondingly substituted furoyl or thenoyl potassium dithiocarbazate with concentrated sulphuric acid at −5° to 10° C. [see J. prakt. Chem. 93, 49 (1916); J. Org. Chem. 23, 1021 (1958); J. Heterocycl. Chem. 19, 542–544 (1982)].

Some of the starting compounds of the formulae IIa and IIb are novel substances that, as intermediates for the preparation of valuable useful end products of the formula I, are a further aspect of the present invention (for example the compounds of Table O).

A preferred method for the use of an active ingredient of the formula I or a nematocidal composition that contains at least one of these active ingredients is the introduction thereof into the soil. For this the locus of the plants is treated with a liquid or solid preparation.

The compounds of the formula I can alternatively, however, be applied to the seed grains (coating) by either soaking the grains in a liquid preparation of the active ingredient or coating them with a solid preparation. Furthermore, in special cases other methods of application are possible, for example the directed treatment of the plant stems, buds or leaves.

Active ingredients of the formula I are customarily used in the form of formulated compositions and may be applied to the areas or plants to be treated simultaneously with or in succession to further active ingredients. These further active ingredients may also include other compositions used in agriculture that in their practical application serve to increase production by promoting the growth of the useful plants, such as fertilizers, herbicides, insecticides, fungicides, molluscicides inter alia, or mixtures of several of these preparations, together with, if desired, other carriers, surfactants or other application-promoting additives customary in the art of formulation.

Suitable carriers and additives may be solid or liquid and correspond to substances appropriate in the art of formulation, such as, for example, natural or regenerated mineral substances, solvents, dispersing agents, wetting agents, tackifiers, thickeners, binders or fertilisers.

The compounds of the formula I are used in unmodified form or, preferably, together with adjuvants customary in the art of formulation. They are processed in known manner, for example, into emulsifiable concentrates, directly sprayable or dilutable solutions, dilute emulsions, wettable powders, soluble powders, dusts, granulates, and encapsulations in, for example, polymeric substances. As with the nature of the compositions, the methods of application, such as spraying, dusting, scattering or pouring, are chosen in accordance with the intended objectives and the prevailing circumstances. Favourable rates of application are generally from 500 g to 6 kg of active ingredient per hectare, preferably from 1 to 4 kg of active ingredient/ha.

The formulations, that is to say the compositions, preparations or formulations containing the active ingredient of the formula I and, where appropriate, a solid or liquid adjuvant, are prepared in known manner, for example by intimate mixing and/or grinding of the active ingredients with extenders, such as, for example, solvents, solid carriers and, where appropriate, surfaceactive substances (surfactants).

Suitable solvents are: aromatic hydrocarbons, preferably the fractions $C_8$–$C_{12}$, such as, for example, xylene mixtures or substituted naphthalenes, phthalic acid esters such as dibutyl or dioctyl phthalate, aliphatic hydrocarbons such as cyclohexane or paraffins, alcohols and glycols and ethers and esters thereof, such as ethanol, ethylene glycol, ethylene glycol monomethyl or monoethyl ether, ketones such as cyclohexanone, strongly polar solvents such as N-methyl-2-pyrrolidone, dimethyl sulphoxide or dimethylformamide, and also vegetable oils which may be epoxidised, such as epoxidised coconut oil or soybean oil, or water.

The solid carriers used, for example for dusts and dispersible powders, are normally powdered natural minerals, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types such as, for example, pumice, broken brick, sepiolite or bentonite, and suitable non-sorbent carrier materials are, for example, calcite or sand. Furthermore, a large number of pre-granulated materials of inorganic or organic nature can be used such as, especially, dolomite or pulverised plant residues.

Depending upon the nature of the active ingredient of the formula I to be formulated, suitable surface-active substances are non-ionic, cationic and/or anionic surfactants having good emulsifying, dispersing and wetting properties. The term surfactants is also to include mixtures of surfactants.

Suitable anionic surfactants can be either so-called water-soluble soaps or water-soluble synthetic surfaceactive compounds.

As soaps there may be mentioned alkali metal, alkaline earth metal or substituted or unsubstituted ammonium salts of higher fatty acids ($C_{10}$–$C_{22}$) such as, for example, the sodium or potassium salts of oleic or stearic acid, or of mixtures of natural fatty acids that can be obtained, for example, from coconut oil or tallow oil. Fatty acid methyltaurin salts should also be mentioned.

More frequently, however, so-called synthetic surfactants are used, especially fatty sulphonates, fatty sulphates, sulphonated benzimidazole derivatives or alkylarylsulphonates.

The fatty alcohol sulphonates or sulphates are generally in the form of alkali metal, alkaline earth metal or substituted or unsubstituted ammonium salts and contain an alkyl radical having from 8 to 22 carbon atoms, alkyl also including the alkyl moiety of acyl radicals, for example the sodium or calcium salt of lignosulphonic acid, of dodecylsulphuric acid ester or of a mixture of fatty alcohol sulphates produced from natural fatty acids. Also included are the salts of sulphuric acid esters and sulphonic acids of fatty alcohol/ethylene oxide adducs. The sulphonated benzimidazole derivatives preferably contain 2 sulphonic acid groups and a fatty acid radical having from 8 to 22 carbon atoms. Alkylarylsulphonates are, for example, the sodium, calcium or triethanolamine salts of dodecylbenzenesulphonic acid, of dibutylnaphthalenesulphonic acid or of naphthalenesulphonic acid/formaldehyde condensation product.

There also come into consideration corresponding phosphates such as, for example, salts of the phosphoric acid ester of an adduct of p-nonylphenol with from 4 to 14 mols of ethylene oxide.

Non-ionic surfactants are especially polyglycol ether derivatives of aliphatic or cycloaliphatic alcohols, of saturated or unsaturated fatty acids and alkylphenols, which derivatives may contain from 3 to 30 glycol ether groups and from 8 to 20 carbon atoms in the (aliphatic) hydrocarbon moiety and from 6 to 18 carbon atoms in the alkyl moiety of the alkylphenols.

Further suitable non-ionic surfactants are the water-soluble adducts of polyethylene oxide with polypropylene glycol, ethylenediamine polypropylene glycol and alkylpolypropylene glycol containing from 1 to 10 carbon atoms in the alkyl chain, which adducts contain from 20 to 250 ethylene glycol ether groups and from 10 to 100 propylene glycol ether groups. The compounds mentioned usually contain from 1 to 5 ethylene glycol units per propylene glycol unit.

There may be mentioned as examples of non-ionic surfactants nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, also come into consideration.

The cationic surfactants are especially quaternary ammonium salts that contain, as N-substituent, at least one alkyl radical having from 8 to 22 carbon atoms and, as further substituents, lower, optionally halogenated alkyl, benzyl or lower hydroxyalkyl radicals. The salts are preferably in the form of halides, methyl sulphates or ethyl sulphates, for example stearyltrimethylammonium chloride or benzyldi-(2-chloroethyl)-ethylammonium bromide.

The agrochemical preparations generally contain from 0.1 to 99% by weight, especially from 0.1 to 95% by weight, of active ingredient of the formula I, from 99.9 to 1% by weight, especially from 99.8 to 5% by weight, of a solid or liquid adjuvant and from 0 to 25% by weight, especially from 0.1 to 25 % by weight, of a surfactant.

Whilst as commercial products concentrated formulations will be preferred, the end user generally uses dilute formulations.

The compositions may also contain further additives, such as stabilisers, anti-foams, viscosity regulators, binders, tackifiers and fertilisers, or other active ingredients for achieving specific effects.

The present invention relates also to such agrochemical compositions.

The following Examples serve to illustrate the invention in detail without implying any limitation.

1. Preparation Examples

Example 1.1: Preparation of

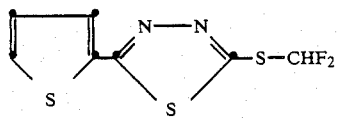

2-difluoromethylthio-5-thienyl-1,3,4-thiadiazole 6.0 g of 2-mercapto-5-thienyl-1,3,4-thiadiazole and 45 ml of dioxan are added, while stirring, to a solution of 2.9 g of potassium hydroxide in 10 ml of water. After the addition of 0.2 g of potassium iodide and 0.1 g of tetrabutylammonium bromide the mixture is heated to 40° C. and, while stirring vigorously, a weak stram of chlorodifluoromethane is introduced for a period of 3 hours. The reaction mixture is then concentrated by evaporation in vacuo. The residue is taken up in methylene chloride and extracted by washing in succession with water and 1N sodium hydroxide solution. Evaporation of the solvent yields the title compound (recrystallised from cyclohexane) in the form of colourless crystals having a melting point of 63°–64° C.

Example 1.2: Preparation of

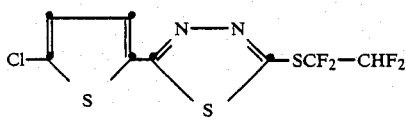

2-(1,1,2,2,-tetrafluoroethylthio)-5-(5'-chlorothien-2'-yl)1,3,4-thiadiazole 0.66 g of potassium hydroxide is added to a solution of 7.1 g of 5-(5'-chlorothien-2'-yl)-2-mercapto-1,3,4-thiadiazole in 60 ml of dimethylformamide, and the mixture is stirred in a pressure vessel. 16 g of tetrafluoroethylene are introduced under pressure and the reaction mixture is heated for 20 hours at 60° C. (10–12.10$^5$ Pa). After cooling and releasing the excess pressure, the solution is poured onto 400 ml of water and the reaction product is extracted with toluene. The residue obtained after distilling off the toluene is 8.7 g of crude title compound which, after recrystallisation from hexane, has a melting point of 66-68° C. (yield 6.8 g).

Example 1.3: Preparation of

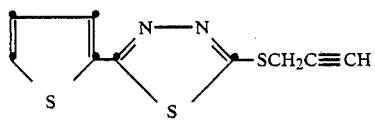

2-propargylthio-5-thien-2-yl-1,3,4-thiadiazole 6 g of 2-mercapto-5-thienyl-1,3,4-thiadiazole are placed in 40 ml of dioxan and stirred for 15 minutes with 3.36 g of potassium tert.-butoxide. Subsequently, 5.9 g of propargyl bromide are added dropwise at 30° C. and the reaction mixture is stirred overnight at room temperature. The salts are filtered off, the filtrate is concentrated by evaporation, the residue is taken up in methylene chloride and the solution is washed with water and then with 1N sodium hydroxide solution. The solvent is removed in vacuo and the residue obtained is 6.1 g of crude title compound which, recrystallised from tert.-butyl methyl ether, yields the title compound having a melting point of 71°–73° C.

The following compounds of the invention may be prepared analogously to the above Preparation Examples and the above-described processes. The listed compounds serve to illustrate the present invention and do not imply any limitation thereof.

TABLE 0

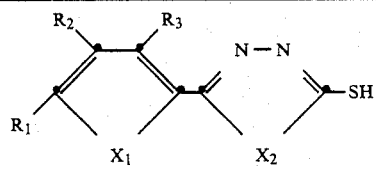

| Comp. No. | R$_1$ | R$_2$ | R$_3$ | X$_1$ | X$_2$ | Physical. Data |
|---|---|---|---|---|---|---|
| 0.1 | H | H | H | S | S | m.p. 186–190° C. |
| 0.2 | H | H | H | S | O | m.p. 197–199° C. |
| 0.3 | H | H | H | O | S | m.p. 225–227° C. |
| 0.4 | Cl | H | H | S | S | m.p. 222–224° C. |
| 0.5 | Br | H | H | S | S | m.p. 220° C. |
| 0.6 | Br | Br | H | S | S | m.p. 218–221° C. |
| 0.7 | CH$_3$ | H | H | S | S | m.p. 236–239° C. |
| 0.8 | H | CH$_3$ | H | S | S | m.p. 213–216° C. |
| 0.9 | H | H | CH$_3$ | S | S | m.p. 200–202° C. |
| 0.10 | Cl | Cl | H | S | S | |
| 0.11 | Cl | Cl | Cl | S | O | |
| 0.12 | Cl | H | H | S | O | m.p. 202–204° C. |
| 0.13 | CH$_3$ | H | H | S | O | m.p. 204–207° C. |
| 0.14 | H | CH$_3$ | H | S | O | |
| 0.15 | H | H | H | O | O | m.p. 171–173° C. |
| 0.16 | Br | H | H | O | O | m.p. 175–177° C. |
| 0.17 | CH$_3$ | H | H | O | O | m.p. 163–166° C. |
| 0.18 | CH$_3$ | H | H | O | S | m.p. 190–194° C. |
| 0.19 | Br | H | H | O | S | m.p. 160° C. and above decomp. |
| 0.20 | Br | Br | H | S | O | m.p. 217–219° C. |
| 0.21 | Cl | H | H | O | O | m.p. 150–155° C. |
| 0.22 | Br | H | H | S | O | m.p. 202–204° C. |

TABLE 1

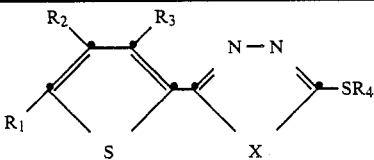

| Comp. No. | R$_1$ | R$_2$ | R$_3$ | X | R$_4$ | Physical Data |
|---|---|---|---|---|---|---|
| 1.1 | H | H | H | S | CHF$_2$ | m.p. 63–64° C. |
| 1.2 | Cl | H | H | S | CHF$_2$ | m.p. 91–92° C. |
| 1.3 | Br | H | H | S | CHF$_2$ | m.p. 92–94° C. |
| 1.4 | CH$_3$ | H | H | S | CHF$_2$ | m.p. 93–95° C. |
| 1.5 | Cl | Cl | H | S | CHF$_2$ | |
| 1.6 | Cl | Cl | Cl | S | CHF$_2$ | |
| 1.7 | Br | Br | H | S | CHF$_2$ | m.p. 100–110° C. |
| 1.8 | H | H | CH$_3$ | S | CHF$_2$ | m.p. 92–94° C. |
| 1.9 | H | CH$_3$ | H | S | CHF$_2$ | m.p. 44–46° C. |
| 1.10 | H | H | H | S | CHF$_2$ | m.p. 56–58° C. |
| 1.11 | Cl | H | H | O | CHF$_2$ | m.p. 73–75° C. |
| 1.12 | Br | H | H | O | CHF$_2$ | |
| 1.13 | H | CH$_3$ | H | O | CHF$_2$ | |
| 1.14 | Cl | H | H | O | CHF$_2$ | |
| 1.15 | Cl | H | H | S | —CF=CFCF$_3$ | m.p. 66–68° C. |
| 1.16 | J | H | H | S | —CF$_2$CHF$_2$ | |
| 1.17 | C$_4$H$_9$(t) | H | H | S | —CHF$_2$ | |
| 1.18 | H | H | H | S | —CH$_2$C≡CH | m.p. 71–73° C. |
| 1.19 | Cl | H | H | S | CH$_2$C≡CH | m.p. 80–83° C. |
| 1.20 | Br | Br | H | S | CH$_2$C≡CH | |
| 1.21 | H | H | CH$_3$ | S | CH$_2$C≡CH | m.p. 82–84° C. |
| 1.22 | CH$_3$ | H | H | S | CH$_2$C≡CH | |
| 1.23 | Cl | H | H | O | CH$_2$C≡CH | m.p. 106–108° C. |
| 1.24 | H | H | H | O | C$_3$H$_7$(i) | n$_D^{24}$ 1.5990 |
| 1.25 | Cl | H | H | S | C$_3$H$_7$(i) | m.p. 87–88° C. |
| 1.26 | Br | H | H | S | C$_3$H$_7$(i) | m.p. 72–73° C. |
| 1.27 | H | H | CH$_3$ | S | C$_3$H$_7$(i) | n$_D^{24}$ 1.6533 |
| 1.28 | Cl | H | H | O | C$_3$H$_7$(i) | m.p. 69–70° C. |
| 1.29 | Br | Br | H | S | C$_3$H$_7$(i) | |
| 1.30 | CH$_3$O | H | H | S | C$_3$H$_7$(i) | |
| 1.31 | Cl | Cl | Cl | S | C$_3$H$_7$(i) | |
| 1.32 | H | H | H | S | CH$_2$CH=CH$_2$ | |
| 1.33 | Cl | H | H | S | CH$_2$CH=CH$_2$ | m.p. 78–80° C. |
| 1.34 | Br | H | H | S | CH$_2$CH=CH$_2$ | |
| 1.35 | Br | Br | H | S | CH$_2$CH=CH$_2$ | |
| 1.36 | Cl | H | H | O | CH$_2$CH=CH$_2$ | m.p. 54–56° C. |
| 1.37 | CH$_3$ | H | H | S | CH$_2$CH=CH$_2$ | |
| 1.38 | CH$_3$ | H | OCH$_3$ | S | CHF$_2$ | m.p. 83–86° C. |
| 1.39 | H | CH$_3$ | H | S | CH$_2$C≡CH | m.p. 96–98° C. |
| 1.40 | H | CH$_3$ | H | S | CH$_3$H$_7$(i) | m.p. 66–68° C. |
| 1.41 | Br | Br | H | O | CHF$_2$ | m.p. 71–73° C. |
| 1.42 | F | H | H | S | CHF$_2$ | |
| 1.43 | F | H | H | O | CHF$_2$ | |
| 1.44 | CH$_3$ | H | H | O | CHF$_2$ | m.p. 65–66.5° C. |
| 1.45 | CH$_3$ | H | H | O | CH$_2$CH$_2$=CH$_2$ | oil |
| 1.46 | CH$_3$ | H | H | O | C$_3$H$_7$(i) | oil |
| 1.47 | CH$_3$ | H | H | O | CH$_2$C≡CH | m.p. 68.5–70° C. |
| 1.48 | Br | H | H | O | CH$_2$C≡CH | m.p. 93–95° C. |
| 1.49 | Br | H | H | O | C$_3$H$_7$(i) | m.p. 66–68° C. |
| 1.50 | Br | H | H | O | CH$_2$CH=CH$_2$ | |
| 1.51 | H | H | H | S | C$_3$H$_7$(i) | n$_D^{20}$ 1.6604 |
| 1.52 | Cl | H | H | O | CF$_2$CHFCF$_3$ | semi-solid |
| 1.53 | Cl | H | H | O | C$_3$H$_7$(i) | m.p. 69–71.5° C. |
| 1.54 | Cl | H | H | O | CH$_2$C≡CH | m.p. 106–108° C. |
| 1.55 | Cl | H | H | O | CH$_2$CH=CH$_2$ | m.p. 54–56° C. |
| 1.56 | Cl | H | H | S | CF$_2$CHFCF$_3$ | solid |

TABLE 2

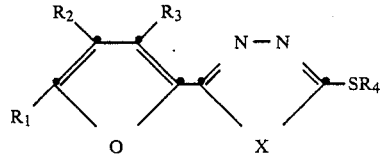

| Comp. No. | R$_1$ | R$_2$ | R$_3$ | X | R$_4$ | Physical Data |
|---|---|---|---|---|---|---|
| 2.1 | H | H | H | S | CHF$_2$ | m.p. 66–68° C. |
| 2.2 | H | H | H | O | CHF$_2$ | m.p. 65–67° C. |
| 2.3 | CH$_3$ | H | H | S | CHF$_2$ | m.p. 49–50° C. |
| 2.4 | CH$_3$ | H | H | S | CH$_2$CH=CH$_2$ | n$_D^{23}$ 1.6384 |
| 2.5 | CH$_3$ | H | H | O | CH$_2$CH=CH$_2$ | |
| 2.6 | CH$_3$ | H | H | S | CH$_2$C≡CH | m.p. 73–75,5° C. |
| 2.7 | CH$_3$ | H | H | O | CH$_2$C≡CH | m.p. 75–77° C. |
| 2.8 | H | H | H | S | CH$_2$C≡CH | m.p. 82–85° C. |
| 2.9 | H | H | H | S | CH$_2$CH=CH$_2$ | m.p. 57–59° C. |
| 2.10 | H | H | H | S | C$_3$H$_7$(i) | oil |
| 2.11 | Br | H | H | S | CHF$_2$ | m.p. 84–86° C. |
| 2.12 | Br | H | H | O | CHF$_2$ | m.p. 53–56° C. |
| 2.13 | H | H | H | S | CF$_2$CHF$_2$ | |
| 2.14 | H | H | H | S | CF=CFCF$_3$ | |
| 2.15 | H | H | H | O | CH$_2$CH=CH$_2$ | oil |
| 2.16 | CH$_3$ | H | H | S | —C$_3$H$_7$(i) | oil |
| 2.17 | CH$_3$ | H | H | O | —CHF$_2$ | oil |
| 2.18 | Cl | H | H | S | —CHF$_2$ | m.p. 76–78° C. |
| 2.19 | CH$_3$ | H | H | O | —CHF$_2$ | oil |
| 2.20 | Cl | H | H | S | —CH$_2$CH=CH$_2$ | m.p. 46–48° C. |
| 2.21 | Cl | H | H | S | —C$_3$H$_7$(i) | oil |
| 2.22 | Cl | H | H | S | —CH$_2$C≡CH | m.p. 70–72° C. |
| 2.23 | H | H | H | O | —C$_3$H$_7$(i) | oil |
| 2.24 | Cl | H | H | O | —CH$_2$C≡CH | m.p. 98–100° C. |
| 2.25 | Cl | H | H | O | —CHF$_2$ | m.p. 50–52° C. |
| 2.26 | Cl | H | H | O | —C$_3$H$_7$(i) | m.p. 57–59° C. |

TABLE 3

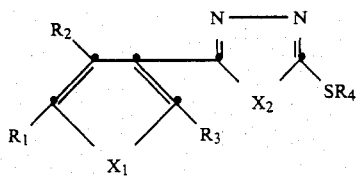

| Comp. No. | R1 | R2 | R3 | X1 | X2 | R4 | Physical Data |
|---|---|---|---|---|---|---|---|
| 3.1 | H | H | H | S | S | CHF2 | |
| 3.2 | H | H | H | O | O | CHF2 | |
| 3.3 | H | H | H | S | O | CHF2 | |
| 3.4 | H | H | H | O | S | CHF2 | |
| 3.5 | H | H | CH3 | S | S | CHF2 | |
| 3.6 | H | H | CH3 | O | S | CHF2 | $n_D^{50}$ 1.6075 |
| 3.7 | CH3 | H | OCH3 | S | S | CHF2 | |
| 3.8 | H | H | CH3 | S | S | CHF2 | |
| 3.9 | H | H | CH3 | S | S | C3H7(i) | |
| 3.10 | H | H | CH3 | S | S | CH2C≡CH | |
| 3.11 | H | H | CH3 | S | S | CH2CH=CH2 | |
| 3.12 | H | H | CH3 | S | S | CF2CHF2 | |
| 3.13 | H | H | CH3 | S | S | CF=CFCF3 | |
| 3.14 | Cl | H | CH3 | S | S | CHF2 | |
| 3.15 | Br | H | CH3 | S | S | CHF2 | |
| 3.16 | Cl | H | H | S | S | CHF2 | |
| 3.17 | CH3 | H | CH3 | S | S | CHF2 | |
| 3.18 | Cl | H | CH3 | O | S | CHF2 | |
| 3.19 | Cl | H | CH3 | O | O | CHF2 | |
| 3.20 | CH3 | H | CH3 | O | O | CHF2 | |
| 3.21 | CH3 | H | CH3 | O | S | CHF2 | m.p. 110–113° C. |
| 3.22 | CH3 | H | CH3 | S | O | CHF2 | |
| 3.23 | H | H | CH3 | O | S | CH2C≡CH | $n_D^{50}$ 1.6359 |
| 3.24 | H | H | CH3 | O | S | CH2CH=CH2 | $n_D^{50}$ 1.6320 |
| 3.25 | Cl | H | Cl | S | O | CHF2 | $n_D^{40}$ 1.5928 |
| 3.26 | Cl | H | Cl | S | S | CHF2 | $n_D^{40}$ 1.6438 |
| 3.27 | Cl | H | Cl | S | O | H | m.p. 225–228° C. |
| 3.28 | H | H | H | O | S | H | m.p. 110° C. and above decomp. |
| 3.29 | H | H | H | O | O | H | m.p. 168–171° C. |
| 3.30 | H | H | H | O | O | CHF2 | oil |
| 3.31 | H | H | H | O | S | CHF2 | m.p. 47–49 |
| 3.32 | Br | H | H | O | S | H | |
| 3.33 | Br | H | H | O | S | CHF2 | |
| 3.34 | Br | H | H | O | O | H | |
| 3.35 | Br | H | H | O | O | CHF2 | |
| 3.36 | H | H | Br | O | S | H | |
| 3.37 | H | H | Br | O | S | CHF2 | |
| 3.38 | H | H | Br | O | O | H | |
| 3.39 | H | H | Br | O | O | CHF2 | |

2. Formulation Examples for liquid active ingredients of the formula I (%=percent by weight)

2.1 Emulsifiable concentrates

| | (a) | (b) | (c) |
|---|---|---|---|
| active ingredient from Tables 1-3 | 25% | 40% | 50% |
| calcium dodecylbenzenesulphonate | 5% | 8% | 6% |
| castor oil-polyethylene glycol ether (36 mols of ethylene oxide) | 5% | — | — |
| tributylphenoyl-polyethylene glycol ether (30 mols of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

2.2 Solutions

| | (a) | (b) | (c) | (d) |
|---|---|---|---|---|
| active ingredient from Tables 1-3 | 80% | 10% | 5% | 95% |
| ethylene glycol monomethyl ether | 20% | — | — | — |
| polyethylene glycol MW 400 | — | 70% | — | — |
| N—methyl-2-pyrrolidone | — | 20% | — | — |
| epoxidised coconut oil | — | — | 1% | 5% |
| benzine (boiling range 160-190° C.) | — | — | 94% | — |

(MW = molecular weight)

The solutions are suitable for use in the form of extremely fine droplets.

2.3 Granulates

| | (a) | (b) |
|---|---|---|
| active ingredient from Tables 1-3 | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent is then evaporated off in vacuo.

2.4 Dusts

| | (a) | (b) |
|---|---|---|
| active ingredient from Tables 1-3 | 2% | 5% |
| highly dispersed silicic acid | 1% | 5% |
| talcum | 97% | — |
| kaolin | — | 90% |

Dusts that are ready for use are obtained by intimately mixing the carriers with the active ingredient.

Formulation Examples for solid active ingredients of the formula I (% = percent by weight)

2.5 Wettable powder

| | (a) | (b) | (c) |
|---|---|---|---|
| active ingredient from Tables 1-3 | 25% | 50% | 75% |
| sodium lignosulphonate | 5% | 5% | — |
| sodium lauryl sulphate | 3% | — | 5% |
| sodium diisobutylnaphthalene-sulphonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is mixed well with the additives and thoroughly ground in a suitable mill. A wettable powder is obtained which can be diluted with water to form a suspension of any desired concentration.

2.6 Emulsifiable concentrate

| | |
|---|---|
| active ingredient from Tables 1-3 | 10% |
| octylphenolpolyethylene glycol ether (4-5 mols of ethylene oxide) | 3% |
| calcium dodecylbenzene-sulphonate | 3% |
| castor oil polyglycol ether (35 mols of ethylene oxide) | 4% |
| cyclohexanone | 30% |
| xylene mixture | 50% |

Emulsions of any desired concentration can be prepared from this concentrate by dilution with water.

| 2.7 Dusts | (a) | (b) |
|---|---|---|
| active ingredient from Tables 1-3 | 5% | 8% |
| talcum | 95% | — |
| kaolin | — | 92% |

Dusts that are ready for use are obtained by mixing the active ingredient with the carriers and grinding in a suitable mill.

| 2.8 Extruder granulate | |
|---|---|
| active ingredient from Tables 1-3 | 10% |
| sodium lignosulphonate | 2% |
| carboxymethylcellulose | 1% |
| kaolin | 87% |

The active ingredient is mixed with the additives, ground and moistened with water. This mixture is extruded and then dried in an air stream.

| 2.9 Coated granulate | |
|---|---|
| active ingredient from Tables 1-3 | 3% |
| polyethylene glycol (MW 200) | 3% |
| kaolin | 94% |
| (MW = molecular weight) | |

The finely ground active ingredient is uniformly applied in a mixer to the kaolin moistened with polyethylene glycol. A dust-free coated granulate is obtained in this manner.

| 2.10 Suspension concentrate | |
|---|---|
| active ingredient from Tables 1-3 | 40% |
| ethylene glycol | 10% |
| nonylphenolpolyethylene glycol ether (15 mols of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. In this manner, a suspension concentrate is obtained from which suspensions of any desired concentration can be prepared by dilution with water.

Biological Examples 3.1 Action against *Meloidogyne incognita*

Eggs of *Meoloidogyne incognita* are mixed into sand. This mixture is then introduced into clay pots each of 200 ml capacity (5000 eggs per pot). On the same day, a 3 week-old tomato plant is planted in each pot and the formulated active ingredient is introduced into the pots by drench application (0.0006% active ingredient based on the volume of soil). The potted plants are then placed in a greenhouse at a temperature of 26°±1° C. and a relative humidity of 60%. After a period of 4 weeks, an evaluation is carried out by examining the plants for the formation of root knot in accordance with the so-called Root Knot Index.

Compounds from Tables 1-3 display a good activity agaist *Meloidogyne incognita* by substantially reducing the root knot formation. Untreated but infected control plants, on the other hand, exhibit pronounced root knot formation (=100%). Thus, for example, compounds Nos. 1.1, 1.2, 1.3, 1.4 and 1.8 inhibit root knot formation in the above test almost completely (0–10% residual attack).

We claim:

1. A compound of the formula

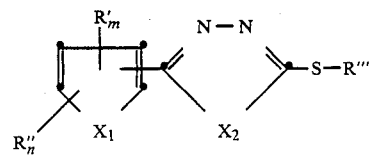

in which

R′ is methyl, chlorine, bromine or methoxy;

R″ is methyl, chlorine or bromine; and

R‴ is $C_1$-$C_3$-alkyl that is substituted by 1 to 3 fluorine atoms, and m is 0 or 1, n is 0 or 1, $X_1$ and $X_2$ independently of the other, is oxygen or sulfur.

2. A compound of claim 1 in which

R′ is methyl, chlorine, bromine or methoxy;

R″ is methyl, chlorine or bromine; and

R‴ is $CHF_2$; and m is 0 or 1.

3. A compound of claim 1 selected from the group consisting of 2-difluoromethylthio-5-thien-2-yl-1,3,4-thiadiazole, 2-difluoromethylthio-5-(5-chlorothien-2-yl)-1,3,4-thiadiazole, 2-difuloromethylthio-5-(5-methylthien-2-yl)-1,3,4-thiadiazole, 2-difluoromethylthio-5-(5-bromothien-2-yl)-1,3,4-thiadiazole, 2-difluoromethylthio-5-thien-2-yl-1,3,4-oxadiazole, 2-difluoromethylthio-5-(chlorothien-2-yl)-1,3,4-oxadiazole, 2-difluoromethylthio-5-(5-methylthien-2-yl)-1,3,4-oxadiazole, 2-difluoromethylthio-5-(furan-2-yl)-1,3,4-thiadiazole, 2-difluoromethylthio-5-(2-methylfuran-3-yl)-1,3,4-thiadiazole, 2-difluoromethylthio-5-(4-methylthien-2-yl)-1,3,4-thiadiazole, and 2-difluoromethylthio-5-(furan-2-yl)-1,3,4-oxadiazole.

4. An anti-nematodal composition comprising an agriculturally-acceptable carrier and an effective nematocidal amount of at least one compound of the formula

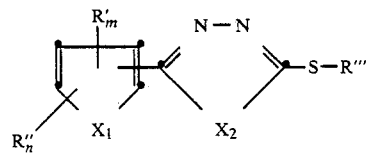

in which

R′ is methyl, chlorine, bromine or methoxy;

R" is methyl, chlorine or bromine; and

R'" is $C_1$–$C_3$-alkyl that is substituted by 1 to 3 fluorine atoms, and m is 0 or 1, n is 0 or 1, $X_1$ and $X_2$ independently of the other, is oxygen or sulfur.

5. A composition of claim 4, which contains 0.1 to 99% of a compound of the formula, 99.9 to 1% of a solid or liquid carrier and 0 to 25% of a surfactant.

6. A composition of claim 5, which contains from 0.1 to 95% of a compound of the formula, 99.8% to 5% of a solid or liquid carrier and from 0.1 to 25% of a surfactant.

7. A method of controlling or preventing an attack on cultivated plants by nematodes, comprising the step of applying a compound of the formula

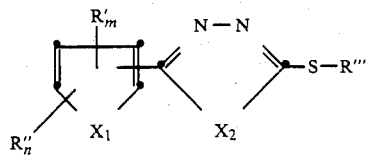

in which

R' is methyl, chlorine, bromine or methoxy;

R" is methyl, chlorine or bromine; and

R'" is $C_1$–$C_3$-alkyl that is substituted by 1 to 3 fluorine atoms, and m is 0 or 1, n is 0 or 1, $X_1$ and $X_2$ independently of the other, is oxygen, or sulfur.

8. The method of claim 7 wherein the nematodes are of a species that parasitizes plants.

9. The method of claim 8 wherein the nematodes are of the genera Meloidogyne, Heterodera or Globodera.

* * * * *